(12) United States Patent
Horn et al.

(10) Patent No.: US 8,609,016 B2
(45) Date of Patent: Dec. 17, 2013

(54) REFOLDABLE BALLOON AND METHOD OF MAKING AND USING THE SAME

(75) Inventors: Daniel J. Horn, Shoreview, MN (US); John J. Chen, Plymouth, MN (US); Calvin Fenn, Monticello, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 2269 days.

(21) Appl. No.: 11/511,156

(22) Filed: Aug. 28, 2006

(65) Prior Publication Data
US 2008/0124495 A1    May 29, 2008

(51) Int. Cl.
*B29C 49/18*    (2006.01)

(52) U.S. Cl.
USPC .......................... 264/530; 264/523; 264/529

(58) Field of Classification Search
None
See application file for complete search history.

(56) References Cited

U.S. PATENT DOCUMENTS

| | | | |
|---|---|---|---|
| 4,490,421 A | 12/1984 | Levy | 428/35 |
| 4,906,244 A | 3/1990 | Pinchuk et al. | 606/194 |
| 4,935,190 A | 6/1990 | Tennerstedt | 264/529 |
| 4,950,239 A | 8/1990 | Gahara et al. | 604/96 |
| 5,226,887 A | 7/1993 | Farr et al. | 604/96 |
| 5,264,260 A | 11/1993 | Saab | 428/35.5 |
| 5,304,340 A | 4/1994 | Downey | 264/521 |
| 5,306,246 A | 4/1994 | Sahatjian et al. | 604/96 |
| 5,318,587 A | 6/1994 | Davey | 606/194 |
| 5,328,468 A | 7/1994 | Kaneko et al. | 604/96 |
| 5,344,400 A | 9/1994 | Kaneko et al. | 604/96 |
| 5,350,361 A * | 9/1994 | Tsukashima et al. | 604/103.07 |
| 5,456,666 A | 10/1995 | Campbell et al. | 604/96 |
| 5,478,319 A | 12/1995 | Campbell et al. | 604/96 |
| 5,500,180 A | 3/1996 | Anderson et al. | 264/532 |
| 5,556,383 A | 9/1996 | Wang et al. | 604/96 |
| 5,714,110 A | 2/1998 | Wang et al. | 264/529 |
| 5,833,657 A | 11/1998 | Reinhardt et al. | 604/96 |
| 6,033,380 A | 3/2000 | Butaric et al. | 604/96 |
| 6,126,652 A | 10/2000 | McLeod et al. | 606/1 |
| 6,146,356 A | 11/2000 | Wang et al. | 604/96 |
| 6,242,063 B1 | 6/2001 | Ferrera et al. | 428/35.2 |
| 6,270,522 B1 | 8/2001 | Simhambhatla et al. | 623/1.11 |
| 6,284,333 B1 | 9/2001 | Wang et al. | 428/35.5 |
| 6,572,813 B1 | 6/2003 | Zhang et al. | 264/519 |
| 6,596,219 B2 | 7/2003 | Schaible et al. | 264/515 |
| 6,946,092 B1 | 9/2005 | Bertolino et al. | 264/512 |
| 2002/0163104 A1 | 11/2002 | Motsenbocker et al. | 264/320 |
| 2003/0083687 A1 | 5/2003 | Pallazza | 606/191 |
| 2003/0130717 A1 | 7/2003 | Hale et al. | |
| 2003/0163157 A1 | 8/2003 | McMorrow et al. | 606/194 |
| 2004/0073165 A1 | 4/2004 | Musbach et al. | |
| 2004/0181252 A1 | 9/2004 | Boyle et al. | |
| 2006/0015134 A1 | 1/2006 | Trinidad | 606/194 |
| 2006/0033241 A1 | 2/2006 | Schewe et al. | 264/402 |

FOREIGN PATENT DOCUMENTS

| | | |
|---|---|---|
| JP | 2003062080 | 3/2003 |
| WO | 2007102941 | 9/2007 |

* cited by examiner

*Primary Examiner* — Monica Huson
(74) *Attorney, Agent, or Firm* — Vidas, Arrett & Steinkraus, P.A.

(57) ABSTRACT

The present invention relates to a method of improving balloon refoldability by molding a preformed balloon into a larger, predetermined shape at a lower temperature and higher pressure than that with which the balloon was originally formed.

19 Claims, 11 Drawing Sheets

REFOLDABLE BALLOON AND METHOD OF MAKING AND USING THE SAME

FIELD OF THE INVENTION

The present invention relates to the field of medical balloons, to catheters using such balloons, and methods of making and using the same.

BACKGROUND OF THE INVENTION

Atherosclerotic cardiovascular disease is common, and is caused by a narrowing of the arterial lining due to atherosclerotic plaques. When plaque builds up, this is referred to in the art as stenosis. One method commonly employed to relieve arterial stenosis resulting from plaque build-up is percutaneous transluminal coronary angioplasty, or balloon angioplasty. PTCA or balloon angioplasty, is a non-invasive, non-surgical means of treating coronary arteries.

This technique consists of inserting a non-inflated balloon catheter into the affected artery. Dilation of the diseased segment of artery is accomplished by inflating the balloon which pushes the atherosclerotic lesion outward, compressing the stenosis and enlarging the arterial diameter.

To effectively expand the lumen and compress the stenosis, it is desirable that the balloon be reliably inflatable to a predetermined diameter when the balloon is infused with fluid. This is so in order to evenly expand the balloon within the affected artery to evenly dilate the vessel, compress and hence compromise the stenosis. Also, it is desirable that the balloon be reliably collapsible to a minimal, radially compact cross sectional shape incident to balloon insertion and withdrawal. This is to facilitate insertion and withdrawal of the balloon in artery. While existing angioplasty balloons are collapsible, they may not always be reliably so, and may flatten into a "pancake" like shape, rather than to a radially compact minimal cross-section, particularly after inflation to a relatively large diameter.

This flattening can increase the possibility that the balloon may interfere with the arterial wall during balloon withdrawal or when being placed across a second stenosis. This pancake-like balloon shape can increase the difficulty of withdrawal after inflation.

Various techniques or balloon constructions have been employed to facilitate the folding of the balloon about the balloon catheter in a uniform manner upon evacuation and deflation of the balloon after use.

One method employed to improve the refoldability of the balloon and improve withdrawal, has been to fold the balloon to form a number of wings. Prior to use, the balloon is typically folded or wrapped about the balloon catheter to fit within and pass through the guide catheter lumen. When inflation fluid is applied to the deflated balloon, the balloon wings or flaps unwrap and the balloon inflates to a fully expanded condition. After inflation, and in the deflated state, the balloon collapses upon itself forming flaps or wings that must be folded or wrapped around the balloon catheter to allow it to be withdrawn from the patient's vasculature after use.

A number of approaches have been employed in forming a balloon that will refold into wings or flaps about the catheter shaft.

One approach has been to construct the balloon of a cylinder of material, such as polyethylene, that is uniform about its circumference but can be heat set after it is wrapped or folded to form curved, overlapping flaps or wings extending from fold lines in a manner described further below. Heat setting of the balloon results in a balloon that when, upon application of negative pressure during deflation, will return fairly closely to its tightly wrapped heat set configuration.

Another approach has been taken to fabricate the balloon itself with fold line structures and flap shapes, particularly for use with balloons formed of stronger polyesters, for example, polyethylene terepthalate (PET).

See, for example, U.S. Pat. Nos. 5,226,887, 5,318,587, 5,456,666 and 5,478,319 for various methods of improving balloon collapsibility after inflation. The entire content of these patents is hereby incorporated by reference herein.

There remains a need, however, for innovative and improved methods for folding balloons and for improved balloon refold.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All US patents and applications and all other published documents mentioned anywhere in this application are incorporated herein by reference in their entirety.

Without limiting the scope of the invention a brief summary of the claimed embodiments of the invention is set forth below. Additional details of the summarized embodiments of the invention and/or additional embodiments of the invention may be found in the Detailed Description of the Invention below.

SUMMARY OF THE INVENTION

In some embodiments, the present invention relates to a method of improving balloon refoldability of expandable medical balloons by molding a preformed expandable medical balloon to an enlarged size as defined by the perimeter of a radial cross-section of the expandable medical balloon.

As used herein, the term "perimeter" shall be used to include the term "circumference" wherein the geometry of the expandable medical balloon is substantially spherical or circular.

In some embodiments, the present invention relates to a method of improving balloon refoldability by radially expanding a pre-formed balloon into an enlarged size as measured by the perimeter of a radial cross-section of the balloon, at a lower temperature than when the balloon was initially formed, i.e. oversizing of the balloon in a subsequent molding step.

In one embodiment, the present invention relates to a method of forming an expandable balloon which includes the steps of radially expanding a balloon preform in a first mold form which has an interior cavity wherein a radial cross-section of the interior cavity of the first mold form is defined by a first perimeter at a first temperature, $T_1$, and a first pressure, $P_1$, to form a pre-formed balloon, and radially expanding the pre-formed balloon in a second mold form having an interior cavity wherein a radial cross-section of the interior cavity of the second mold form is defined by a second perimeter which is larger than the first perimeter of the first mold form at a second temperature, $T_2$ and a second pressure, $P_2$ wherein $T_2 < T_1$. Suitably, $P_2 > P_1$.

In another embodiment a pre-formed balloon having a first perimeter is inflated with inflation media and heat set blades are applied to said balloon simultaneously while releasing the inflation media. The pre-formed balloon is suitably inflated to a second larger perimeter, prior to application of heat set blades and release of the inflation media.

The balloon may be set into any geometric shape desired including, for example, a two wing, three wing, four wing structure, a star structure, i.e. typically having five or more points, triangle, rectangle, square, etc.

The present invention can be employed for both POBA (plain old balloon angioplasty) and for balloons used in SDS (stent delivery systems).

These and other aspects, embodiments and advantages of the present invention will become immediately apparent to those of ordinary skill in the art upon review of the Detailed Description and claims to follow.

DETAILED DESCRIPTION OF THE INVENTION

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, unless otherwise indicated, identical reference numerals used in different figures refer to the same component.

The expandable balloons according to the invention are expandable from a folded configuration for insertion into a patient's body lumen, expanded to an enlarged diameter to provide medical treatment, with a fluid, for example, and after treatment, being evacuated and deflated wherein the balloon is revertible into a folded configuration of a predetermined shape.

The balloons according to the invention have a first molded state prior to expansion or deflation, often referred to in the art as a static state, at least one expanded state of an enlarged diameter, and a deflated state. The term "deflated" may refer to a medical balloon which has been evacuated or deflated from its static state. Of course, a balloon may also be deflated from its fully expanded state, but remains in a state of expansion, between that of a fully expanded state and a deflated state.

The selected inflation pressures to expand the balloon to its enlarged diameter may vary depending on the type of balloon employed, the application for which the balloon is employed, the type of balloon material employed, the wall thickness, number of layers employed, and whether or not there is a reinforcement material such as fibers or braids employed, etc. Reinforcement materials can increase balloon inflation pressures. Suitable inflation pressures may range from about 8 to about 30 atmospheres.

Balloons typically have a rated pressure which is defined as the highest intended use pressure below that of the burst pressure of a balloon. Rated pressure is also dictated by repeat inflation performance. Balloons employed in peripheral vessels, for example, may have rated burst pressures of about 12-14 atmospheres while balloons used in the coronary vessels may have burst pressures of about 16-21 atmospheres. These examples are intended for illustrative purposes only, and not as a limitation on the scope of the present invention. Modifying the design of the balloon, such as with reinforcement, for example braiding, may lead to higher rated burst pressures.

The balloons according to the invention may be formed using any conventional balloon forming techniques. Balloons are typically formed by expanding a segment of extruded polymer tubing into a balloon mold. Balloon formation is described, for example, in U.S. Pat. Nos. 4,490,421, 5,264,260, 4,906,244, 4,935,190, 5,304,340, 5,306,246, 5,328,468, 4,950,239, 5,500,180, 5,556,383, 5,714,110, 6,146,356, 6,270,522, 5,344,400, 5,833,657, 6,572,813 and 6,946,092 each of which is incorporated by reference herein in their entirety.

In some embodiments, the present invention relates to a method of providing a balloon with improved refoldability after inflation to an enlarged radial cross-section. Suitably for improved refoldability, as will be described in more detail below, the balloons formed according to the present method, have at least one second molded configuration which has a non-cylindrical geometry. More suitably, for improved balloon refoldability, the balloons formed according to the present method, have at least one second molded configuration, which has a winged configuration.

The method generally includes the steps of providing a pre-formed balloon, and radially expanding the preformed balloon in a mold form wherein a radial cross-section of the cavity of the mold form is defined by a perimeter which is larger than that with which the preformed balloon was formed.

The temperature, $T_2$, employed in the second molding step is suitably lower than the temperature, $T_1$, at which the preformed balloon was originally formed. More suitably, the temperature, $T_2$, is between the sterilization temperature of the balloon, $T_3$, and the temperature of original balloon formation, $T_1$. Suitably, the pressure, $P_2$, during the oversize molding step, is greater than the pressure, $P_1$, at which the preformed balloon was originally formed.

Any suitable method of balloon formation can be used to initially form the preformed balloon. A typical method may include extruding a polymeric tubular parison having a first outer diameter, and then radially expanding the tubular parison to a second outer diameter, optionally with a concurrent or intermediate axial stretching step.

Temperatures employed during balloon formation may typically range between about 90° C. and about 100° C. and molding pressures between about 300 psi and 500 psi, and more suitably about 350 psi and about 450 psi. These values are intended for illustrative purposes only, and of course, temperatures and pressures may be adjusted depending on the balloon material employed, for example.

More specifically, using the method according the present specification, the balloon can be formed vial radial expansion in a first mold form having an internal cavity wherein a radial cross-section of the internal cavity of the mold form is defined by a first perimeter to form a pre-formed balloon, and then placing the preformed balloon in a second mold form having an internal cavity wherein a radial cross-section of the internal cavity is defined by a second larger perimeter, than that of the first mold form. The temperature employed in the second molding step is suitably lower than that of the first molding step, but higher than the temperature at which the balloon is sterilized. Thus, the memory of the balloon shape after the first molding step is not destroyed by the second molding step or during sterilization, and the memory of the balloon shape after the second molding step is not destroyed during sterilization.

Suitably, for improved balloon refoldability, the second mold form has an internal cavity wherein a radial cross-section of the internal cavity is defined by a second perimeter which has a non-cylindrical geometry, and more suitably, the second mold form has an internal cavity wherein a radial cross-section of the internal cavity is defined by a second perimeter which has a winged configuration. Thus, in some embodiments, memory of the balloon shape after the second molding step facilitates balloon refold and makes withdrawal from a patient's body lumen easier.

The temperature, $T_2$, and pressure, $P_2$, employed during the second molding step may be selected based on the temperature, $T_1$, and pressure, $P_1$, employed during the first molding step. Suitably, $T_2$ is about 10% to about 50% lower than the $T_1$, and more suitably $T_2$ is about 10% to about 30% lower than $T_1$. Most suitably, the temperature, $T_2$, employed during the second molding step is between about 70° C. and 80° C. For purposes of this application, the percentages shall be based on a range from 0° C. to $T_1$.

The pressure, $P_2$, employed during the second molding step may be the same as, or different than, the pressure, $P_1$, employed during balloon formation. Suitably, the pressure, $P_2$, of the second molding step is about 10% to about 50% higher than the pressure employed in the first molding step, $P_1$, and more suitably, $P_2$ is about 10% to about 30% higher than $P_1$. Most suitably, $P_2$ is about 450 psi and about 500 psi.

The values provided for temperature and pressure are intended for illustrative purposes only, and not as a limitation on the scope of the present invention, and may be varied where suitable.

While the expandable balloons described herein may take on many geometric configurations, there will be described herein, some specific embodiments of the invention.

Figure 1:
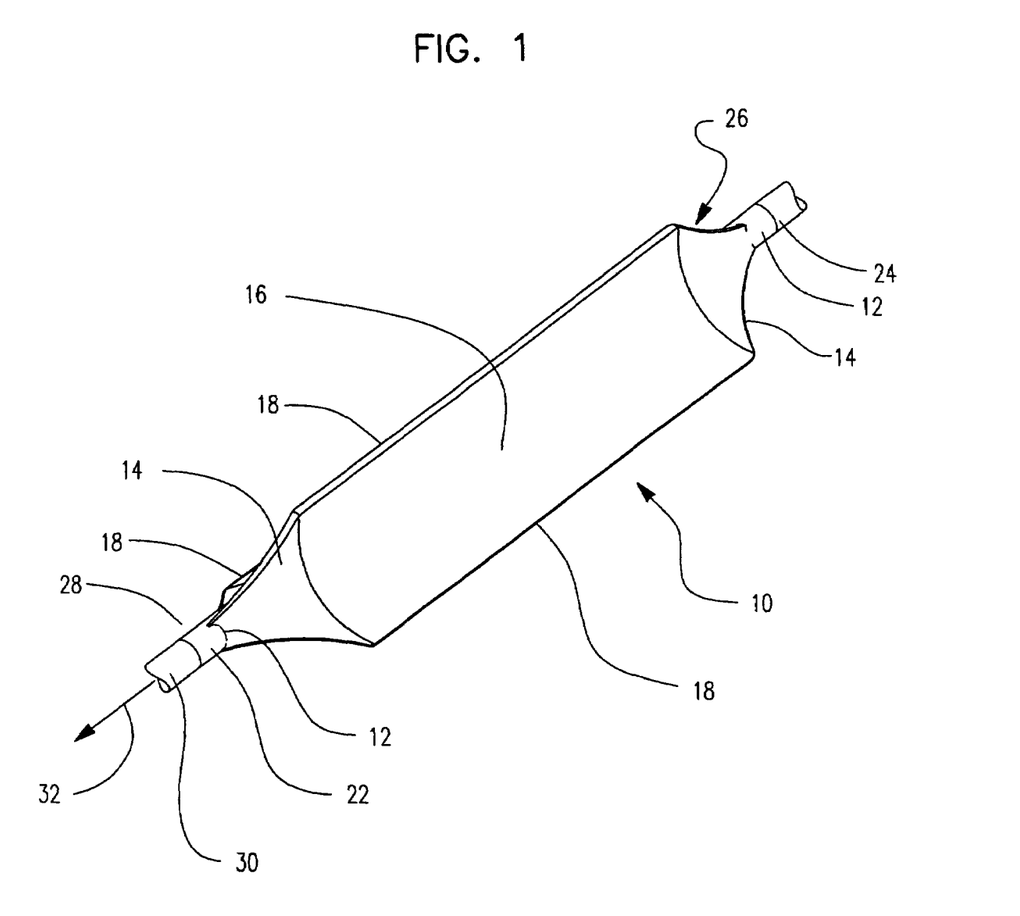
FIG. 1 is a perspective view of one embodiment of a balloon according to the invention.

Turning now to the figures, FIG. 1 illustrates generally at 10, a perspective view of a balloon in a deflated state disposed about the distal end of a catheter having an inner shaft 22 and an outer shaft 24 and an inflation lumen (not shown) extending there between. Fluid may be supplied to the balloon through the inflation lumen to expand the balloon, and upon negative pressure, the balloon can be deflated. The balloon is shown in a deflated configuration, and has not yet been folded or wrapped about the catheter assembly. In this embodiment, balloon 10 has waist portions 12, cone portions 14 and a body portion 16. Balloon 10 is shown in a deflated state having three wings 18. These wings may extend into the cone portions 14 and the waist portions 12, such that the waist portions 12 will have wing marks. The amount that the wings extend into these portions can be controlled to various degrees using the molding method according to the invention.

The configuration shown in FIG. 1 is for illustrative purposes only, and is not intended as a limitation on the scope of the present invention. As noted above, balloon 10 can have any number of wings including 2, 3, 4, 5, 6 or more, and can have other geometric configurations as well including triangle, rectangle, square, etc. Wings 18 may also have other than a triangular shape. See, for example, commonly assigned copending U.S. Patent Publication No. 2006/0015134, the entire content of which is incorporated by reference herein.

Balloon 10 is secured to the inner catheter shaft 22 at its distal end 28 and secured to the outer catheter shaft 24 at its proximal end 26. Inner catheter shaft 22 may define a guide wire lumen 30 for accommodating a guide wire used to steer and manipulate balloon 10 within a patient's lumen during a medical procedure such as angioplasty or for stent delivery.

Balloon 10 is further shown having a longitudinal axis 32 wherein if the balloon is folded, the wings 18 may be wrapped about the longitudinal axis 32. Any conventional balloon folding apparatuses and techniques may be employed in folding or wrapping the balloons according to the invention. Conventional technologies typically employ a number of hard die-like structures which are moved radially inward toward the center of a partially expanded balloon. Negative pressure is applied to the balloon, such as by vacuum, during the folding process. The balloon is typically placed in a holding fixture, and then maintained in a partially expanded state until the dies have reached the end of their stroke. A vacuum is then applied to deflate the balloon and form wings that conform to the configuration of the dies. The wings may then be wrapped or rolled about the circumference of the balloon. For a three wing apparatus, the dies of the folding apparatus may be circumferentially spaced at 120 degree intervals about the balloon. Examples of balloon folding apparatuses are found in commonly assigned copending U.S. Patent Publication Nos. 2003/083687 and 2003/0163157, the entire contents of which are incorporated by reference herein. Other examples include U.S. Pat. Nos. 5,350,361, 6,126,652, 6,033, 380 and 2002/163104, each of which is incorporated by reference herein in their entirety.

Figure 2:
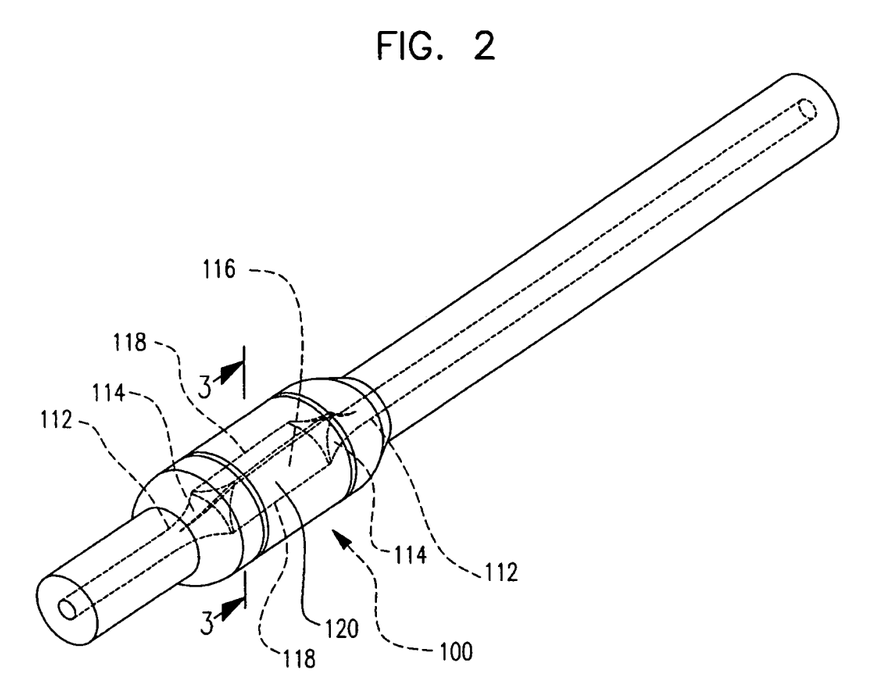
FIG. 2 is a perspective view of a balloon mold form which may be used in accordance with the invention with internal parts shown in hidden line.

To facilitate balloon folding, once the balloon according to the invention has been formed, it may be placed in a second mold. The balloon formed according to the method described herein, can retain the shape acquired as a result of the first balloon forming step, and can retain the shape acquired as a result of the second balloon forming step. One embodiment of a mold 100 which can be employed in a second forming step according to the invention is shown in FIG. 2 as a perspective view with internal parts shown in hidden line. It is the inner surfaces of the mold form cavity 120 which defines the balloon structure. The cavity 120 of the balloon mold form is shown having region 116 which corresponds to the balloon body, regions 112 which corresponds the balloon waist regions, regions 114 which correspond to the balloon cone regions. The mold cavity is shown having three wing regions 118. A significant portion of region 112 of cavity 120 is removed from the balloon after all formation steps have been completed.

Figure 3:
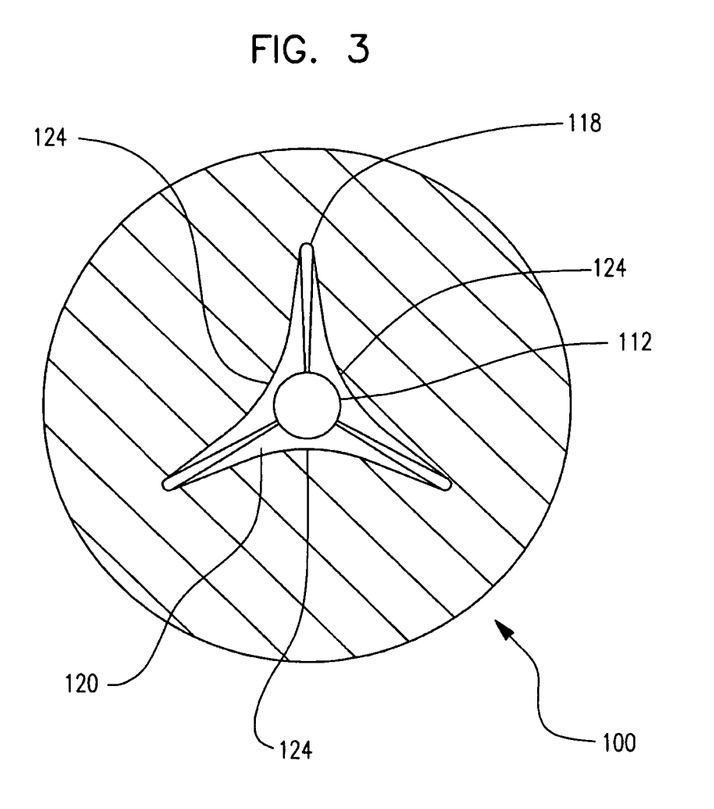
FIG. 3 is radial sectional view taken along lines 3-3 in FIG. 2.

FIG. 3 is a radial sectional view taken at lines 3-3 in FIG. 2. Perimeter 124 of the mold form cavity 120 defines the balloon shape. In this particular embodiment, a structure having three wings 118 is defined by the perimeter 124 of the mold form cavity 120.

The perimeter of this mold form is larger than that of the mold form employed in a first molding step. Suitably, the perimeter is about 5% to about 30% larger than that of the mold form employed in a first molding step.

Figure 4:
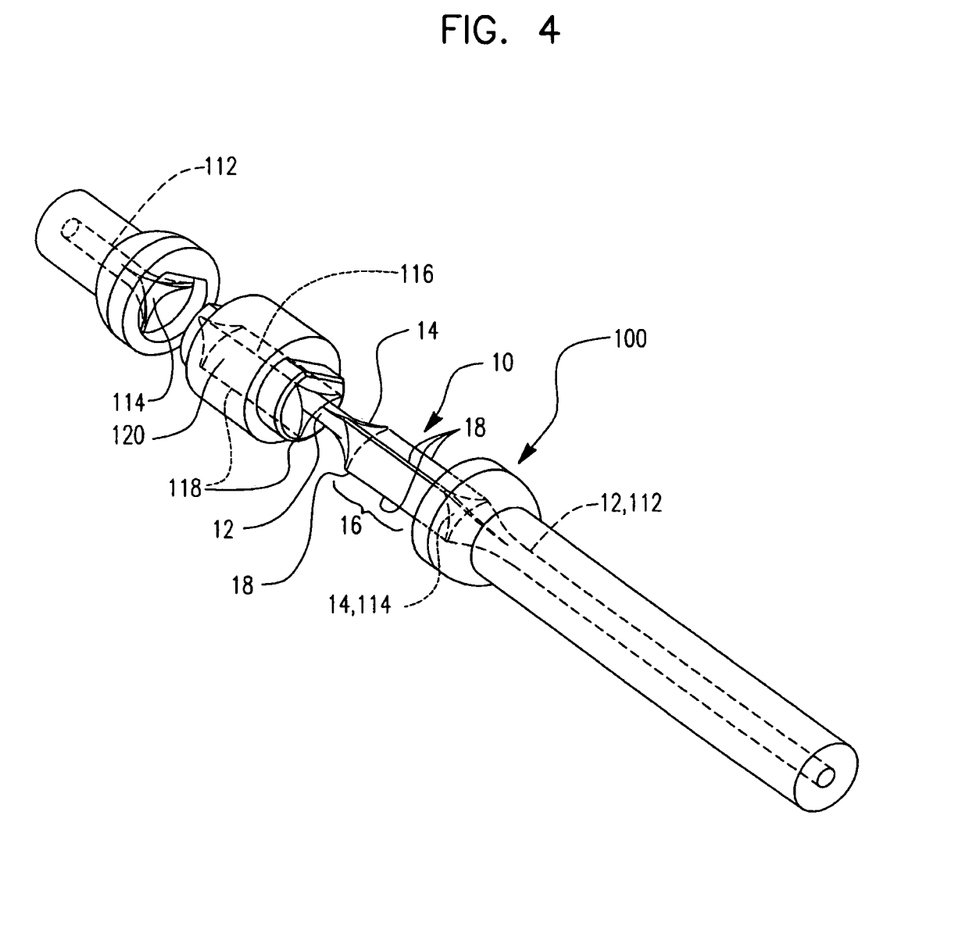
FIG. 4 is a perspective view of a balloon mold form similar to that shown in FIGS. 2 and 3 with parts exploded and a balloon in accordance with the invention.

The mold form 10 may be configured to open or disassemble, to facilitate removal of the formed balloon. FIG. 4 is an alternative exploded perspective view of a balloon mold similar to that in FIGS. 2 and 3 in combination with a balloon 10. Balloon 10 is shown partially released from cavity 120 of mold form 100 and is shown having waist 12, cone 14 and body 16, and having three wing regions 18. This structure corresponds to the internal cavity 120 of mold form 100. The body region 116 of the internal cavity of the mold form can be seen with five wing regions 118 as well. The outer surface of the mold form generally follows the contours of the interior cavity of the mold form. However, the outer surface of the mold form is irrelevant to the resultant balloon configuration.

The mold may be constructed of any suitable mold material including, but not limited to, aluminum, titanium, stainless steel, clad copper, etc. Glass and ceramic may also be employed. The mold is suitably formed of a heat transmissible material. Preferably, the material from which the mold form is made also provides highly polished or glassy internal surfaces. Composite and laminate materials may also be employed herein.

Figure 5:
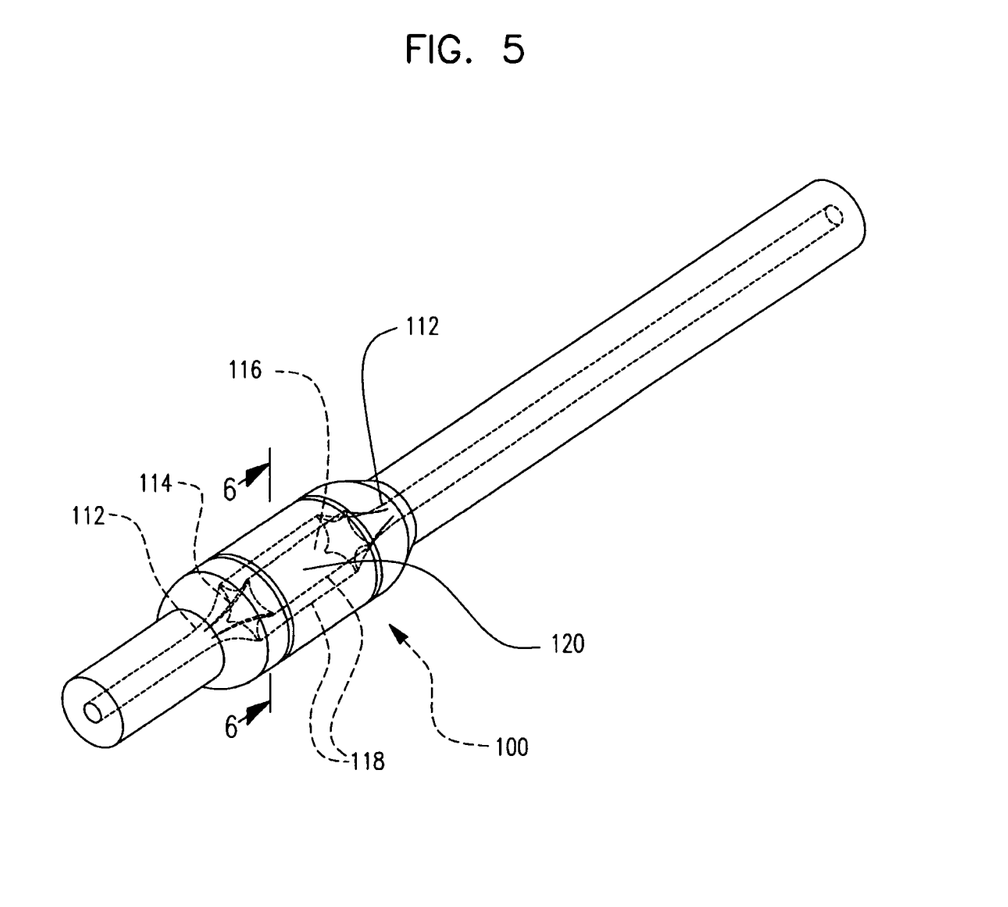
FIG. 5 is a perspective view of an alternative balloon mold form in accordance with the present invention.

FIG. 5 illustrates another embodiment having a mold form 100 having an internal cavity corresponding to a five-winged balloon structure. The internal surfaces of the mold form 100 are shown in phantom. Mold form 100 has an internal cavity 120 which defines waist regions 112, cone regions 114, a body region 116 and wing regions 118. In this embodiment, the wing regions 118 extend into the cone regions 114 as well.

Figure 6:
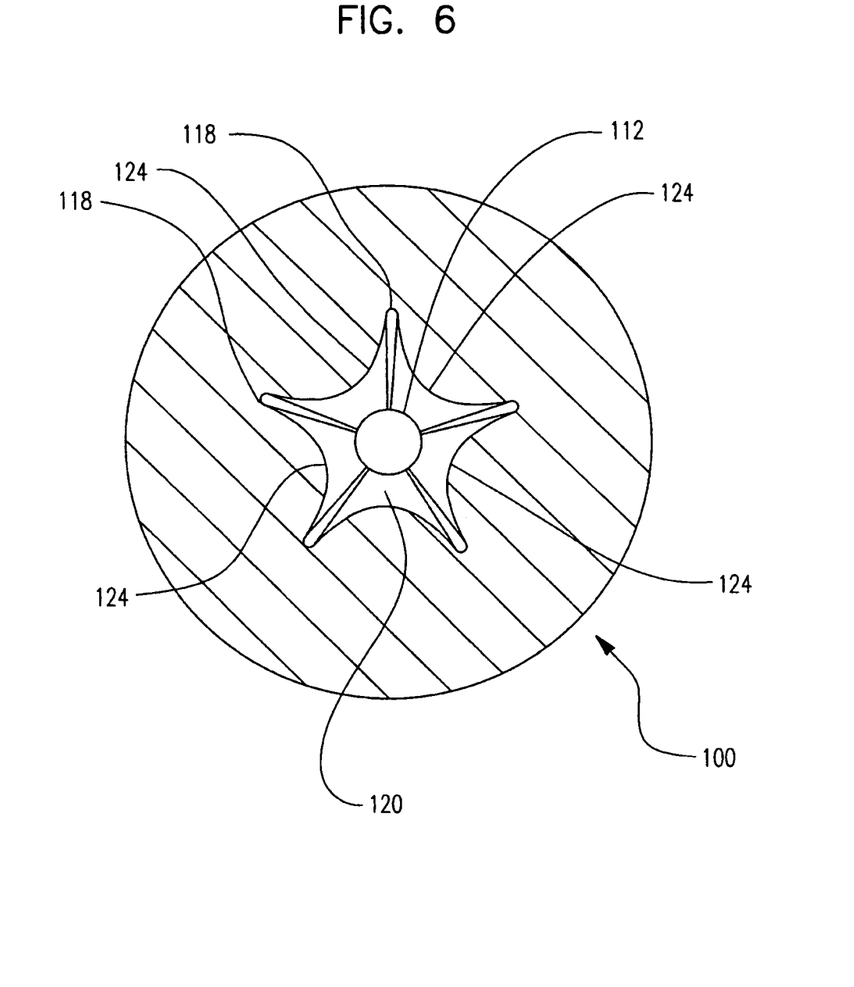
FIG. 6 is a radial sectional view taken along lines 6-6 in FIG. 5.

FIG. 6 is a radial cross-section taken at section 6-6 in FIG. 5 which more clearly illustrates the structure of the internal cavity 120. In this embodiment, the perimeter 124 of the internal cavity 120 defines a five-point star configuration. The resultant balloon will thus have a five-point star, i.e. five winged, configuration.

Figure 7:
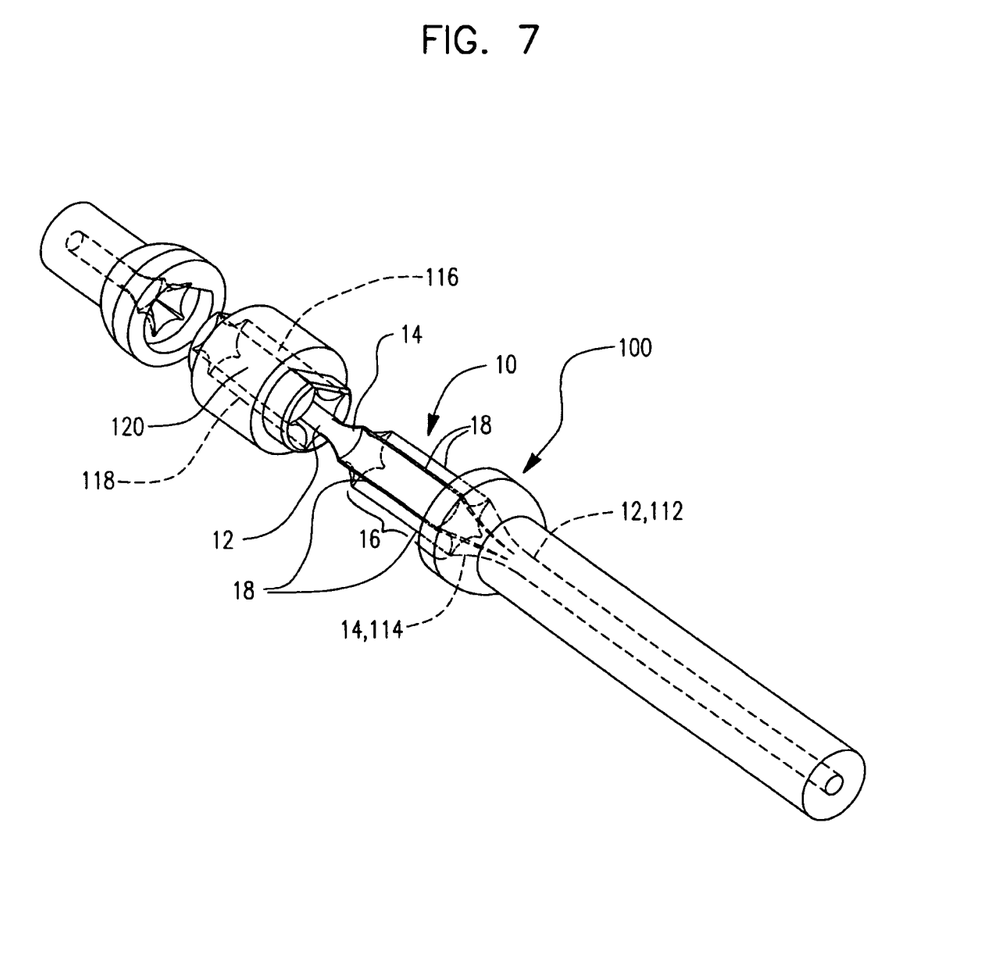
FIG. 7 is a perspective view of a balloon mold form similar to that shown in FIGS. 5 and 6 with parts exploded and a balloon in accordance with the invention.

FIG. 7 is a partial perspective exploded view of a mold form 100 shown in combination with a five-winged balloon 10 being released from mold form 100. Again, in this embodiment, the mold form is configured to open and disassemble to facilitate removal of the formed balloon. Balloon 10 has cone portions 114, waist portions 112 and a body portion. Balloon 10 has five wings 118. The body region 116 of the internal cavity of the mold form can be seen with five wing regions 118 as well.

The mold form according to the invention may be further provided with suitable sensors, such as thermocouples, to monitor the temperature. Such sensors may feed back to an automated heating control system.

Other systems may employ a heated fluid bath. In systems where a heated fluid bath as primary means of heating, thermal transfer therefrom can be further facilitated by agitation of the fluid and/or vibration of the bath apparatus, for instance by ultrasonic vibration.

The balloons according to the invention may be formed from any suitable balloon material which can be molded as described. Suitable classes of materials include, but are not limited to, polyolefins, polyamides (i.e. nylons), polyesters and copolyesters, polyurethanes, polyethers, polyimides, polycarbonates, etc. Copolymers are suitable for use as well.

Examples of suitable polyesters include, but are not limited to, polyethylene terephthalate (PET), polybutylene terephthalate (PBT), polyethylene naphthalate (PEN), etc.

HYTREL®, polyester-ester elastomers available from DuPont Wilmington, Del. and ARNITEL® polyester-esters and polyether-esters available from DSM Engineering Plastics—Americas in Evansville, Ind. may also be employed herein. These polymers are available in different grades depending on desired balloon properties.

Block copolymer elastomers, such as poly(ether-block-amide) block copolymers available under the tradename of PEBAX® from Arkema in Paris, France, may be employed herein. PEBAX® is available in different grades, for example, 6333, 7033 and 7233 are all suitable depending on the balloon properties desired.

Suitable polyamides include, but are not limited to, nylon 6, nylon 10, nylon 11 and nylon 12.

Polyurethanes are available commercially under the tradenames of ISOPLAST® and PELLETHANE® from Dow Chemical Co. in Midland, Mich.

These and other suitable balloon materials are described in U.S. Pat. Nos. 4,906,244, 5,556,383 and 6,270,522, the entire contents of which are incorporated by reference herein. The present invention is not limited by the polymeric material which may be employed herein.

Reinforcement materials such as liquid crystal polymers may also be employed herein. Liquid crystal polymers are described for use in balloons in U.S. Pat. Nos. 6,242,063, 6,284,333 and 6,596,219, the entire contents of which are incorporated by reference herein.

The above lists are intended for illustrative purposes only, and not intended to limit the scope of the present invention. Selection of balloon materials is known to those of skill in the art.

Figure 8:
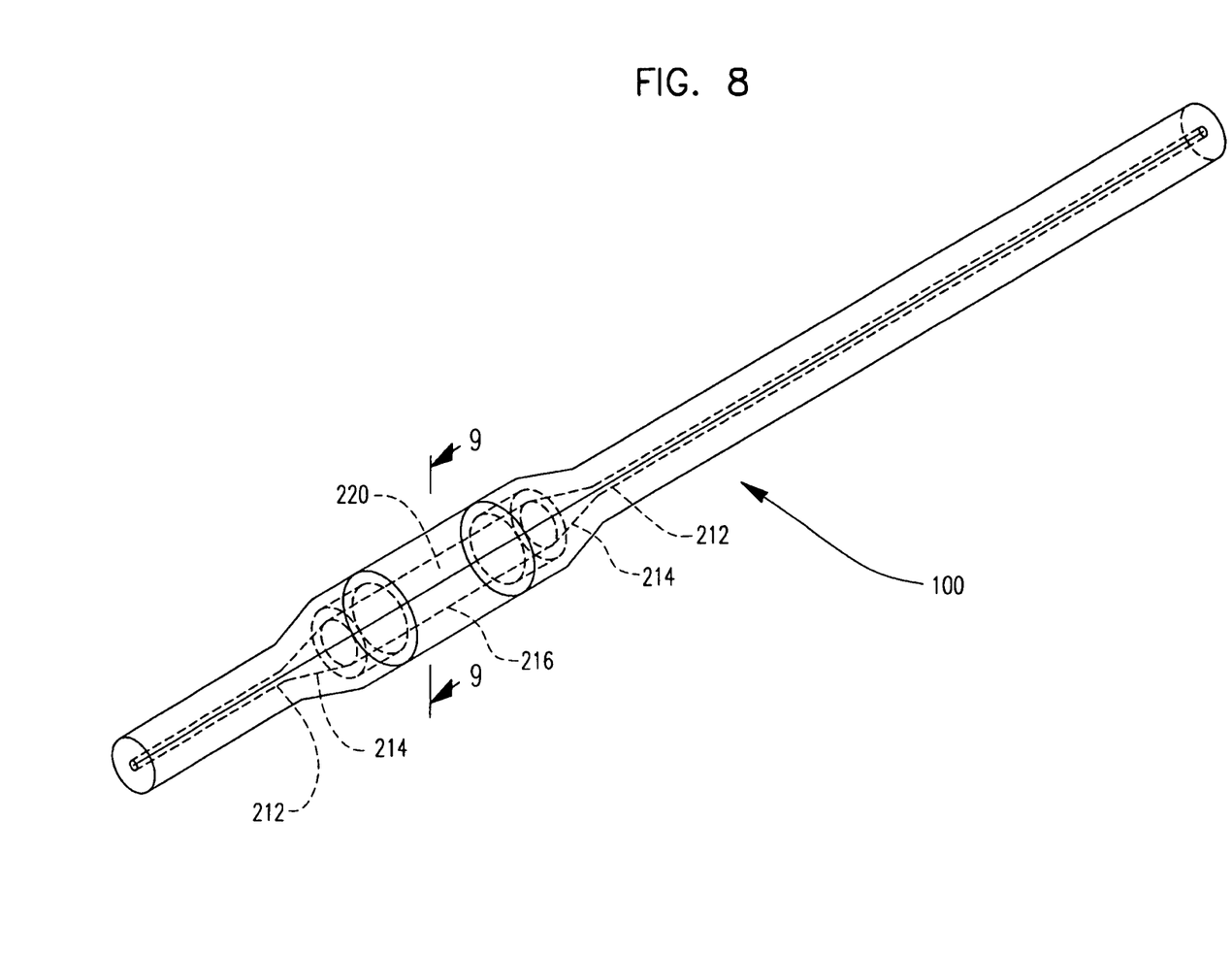
FIG. 8 is a perspective view of a conventional mold form which may be employed in forming the preformed balloon in accordance with the invention with internal parts shown in hidden line.
Figure 9:
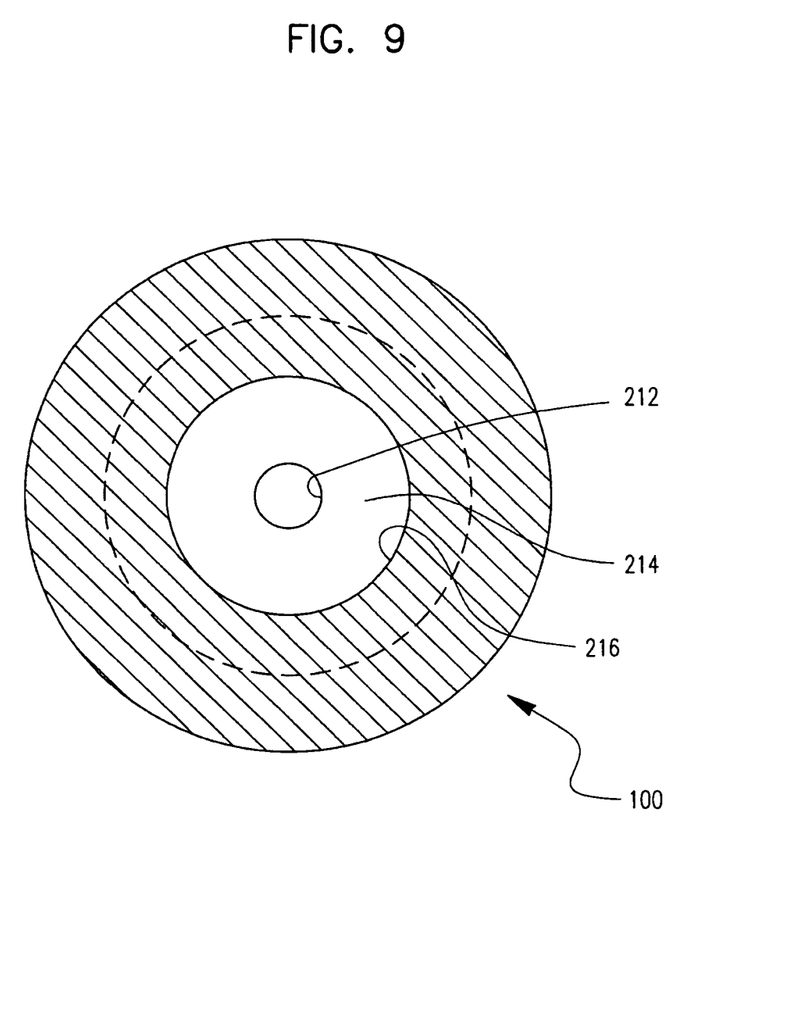
FIG. 9 is a radial cross-section taken at lines 9-9 in FIG. 8.

In one embodiment, a tubular parison or balloon preform of PEBAX® 7233 is extruded and placed in a first mold form wherein the body region of the mold form corresponds to that of substantially spherical or circular balloon having a diameter of 4.0 mm and a circumference of $\pi d$ or $4\pi$ as measured at the central body portion. A mold form 100 which can be employed in this first molding step is shown in FIGS. 8-11. FIG. 8 is a perspective view with internal parts shown in hidden line. Mold form 100 has an internal cavity 220. Internal cavity 220 has a region 216 which corresponds to a balloon body, regions 214 which correspond to balloon cones and regions 212 which correspond to balloon waists. A significant portion of the latter region 212 is removed once all balloon formation steps have been completed. Region 216 of internal cavity 220 defines a substantially circular shape. FIG. 9 is a radial cross-section taken at section 9-9 in FIG. 8.

Figure 10:
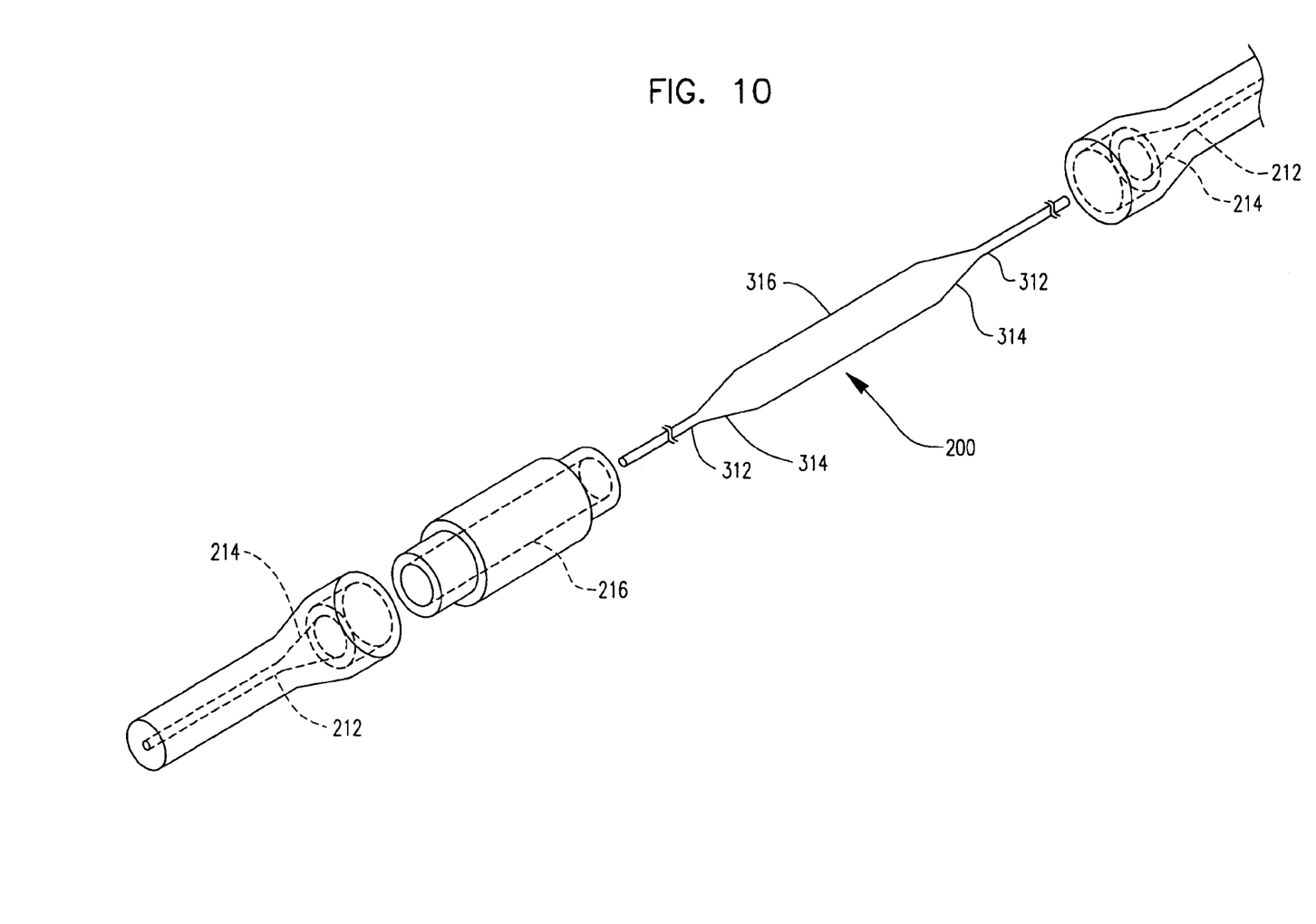
FIG. 10 is a perspective view of a balloon mold form similar to that shown in FIGS. 8 and 9 with parts exploded and a preformed balloon in accordance with the invention.
Figure 11:
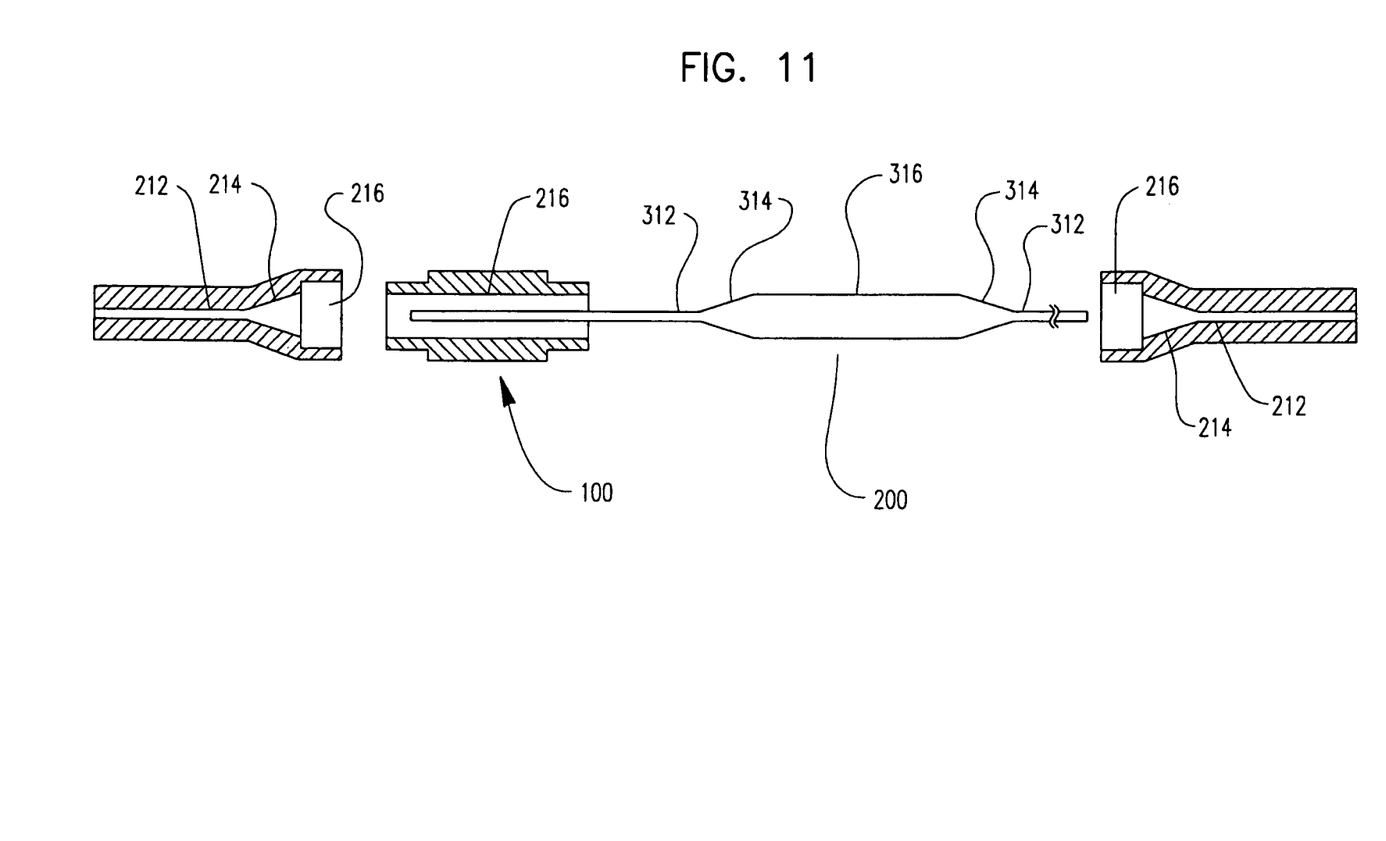
FIG. 11 is an enlarged cross-sectional side view of the balloon mold form 100 shown in FIGS. 8-10 with parts exploded and a preformed balloon 200 in accordance with the invention.

FIG. 10 is a perspective view of a balloon mold form 100 similar to that shown in FIGS. 8 and 9 with parts exploded and a preformed balloon 200 in accordance with the invention. Balloon 200 has a substantially circular shape in body region 316. FIG. 11 is an enlarged side view of the balloon mold form 100 with parts exploded and a preformed balloon 200 in accordance with the invention.

This example of a mold form is intended for illustrative purposes only, and not as a limitation on the scope of the present invention. Other suitable mold forms which may be employed in this step can be found in U.S. Patent Publication No. 2006/0033241, the entire content of which is incorporated by reference herein. In this step, the temperature, $T_1$, is suitably higher than that which will be employed in the subsequent molding step described below. In this embodiment, the balloon is radially expanded at a temperature, $T_1$, of about 95° C. to form the preformed balloon.

Mold temperatures for this step may suitably be in the range of about 90° C. and about 100° C., although temperatures may vary depending on the type of material selected for forming the balloon.

The pressure employed for the first molding step in this embodiment is about was about 400 psi and 40 grams of tension. Pressures may range from about 300 psi to about 500 psi, and more suitably about 350 psi to about 450 psi.

The preformed balloon is then removed from the first mold form and placed in a second mold form of the type described in FIGS. 2-7. This second mold form has a slightly larger diameter size of 4.5 mm. For the embodiments shown in FIGS. 2-7, the diameter may be closely approximated by using the value of the perimeter, which is the sum of all of the arc lengths of the three or five winged star configuration, divided by π. However, this calculation for the diameter may not be appropriate for all configurations. The perimeter of a radial cross-sectional of the second mold form may be about 5% to about 30% greater than the perimeter of a radial cross-sectional of the first mold form. In this particular example, the perimeter of the balloon produced after the second molding step is about 12.5% greater than the perimeter (circumference) of the balloon produced after the first molding step.

The preformed balloon was radially expanded into this second mold form at a temperature of about 75° C. As discussed above, the temperature, $T_2$, of the second molding step is suitably about 10% to about 30% less than that of $T_1$. In this example, $T_2$ is about 90-75/90 or about 17% less than $T_1$. The temperature, $T_2$, of the second molding step may range from about 40° C. to about 90° C., suitably about 70° C. to about 90° C., providing that it is between about 10% and 50%, and more suitably about 10% and about 30% lower than the temperature of the first molding step, $T_1$.

The pressure employed for the second molding step was about 500 psi and 250 grams of tension. In this embodiment, the pressure, $P_2$, employed in the second molding step is about 25% greater than the pressure, $P_1$, employed in the first molding step.

The balloon may then be sterilized at a temperature $T_3$, which is suitably less than $T_2$. Typical sterilizations may be accomplished at temperatures of between about 50° C. and about 60° C. A commonly employed method uses ethylene oxide gas (EtO) for balloon sterilization. Such sterilization techniques are known in the art.

The above examples and disclosure are intended to be illustrative and not exhaustive. These examples and description will suggest many variations and alternatives to one of ordinary skill in this art. All these alternative and variations are intended to be included within the scope of the claims, where the term "comprising" means "including, but not limited to." Those familiar with the art may recognize other equivalents to the specific embodiments described herein which equivalents are also intended to be encompassed by the claims.

The invention claimed is:

1. A method of forming an expandable balloon for a medical device, the method comprising the steps of:
    providing a balloon preform;
    placing said balloon preform in a first mold form, the first mold form having an interior cavity wherein a radial cross-section of the interior cavity of the first mold form is defined by a first perimeter;
    radially expanding said balloon preform in said first mold form at a temperature, $T_1$, and a pressure, $P_1$, to form a pre-formed balloon, the pre-formed balloon having a circular cross-sectional shape;
    placing said pre-formed balloon in a second mold form, the second mold form having an interior cavity wherein a radial cross-section of the interior cavity of the second mold form is defined by a second perimeter which is larger than the first perimeter of the first mold form;
    radially expanding said pre-formed balloon in the second mold form at a temperature, $T_2$, wherein $T_2<T_1$ and a pressure, $P_2$ to form a balloon having a polygonal geometric cross-sectional shape with a perimeter that is larger than that of the preformed balloon.

2. The method of claim 1 wherein the $P_2>P_1$.

3. The method of claim 1 further comprising the step of sterilizing said expandable balloon at a temperature, $T_3$ wherein $T_3<T_2$.

4. The method of claim 1 wherein $T_1$ is about 90° C. and about 100° C.

5. The method of claim 1 wherein $T_2$ is about 70° C. and about 80° C.

6. The method of claim 3 wherein $T_3$ is about 45° C. and about 60° C.

7. The method of claim 1 wherein $P_1$ is about 350 psi and about 450 psi.

8. The method of claim 1 wherein $P_2$ is about 450 psi and 500 psi.

9. The method of claim 1 wherein $T_2$ is about 10% to about 50% lower than the first temperature.

10. The method of claim 1 wherein $T_2$ is about 10% to about 30% lower than the first temperature.

11. The method of claim 1 wherein $P_2$ is about 10% to about 50% higher than the first pressure.

12. The method of claim 1 wherein $P_2$ is about 10% to about 30% higher than the first pressure.

13. The method of claim 1 wherein the second mold form has an interior cavity, the interior cavity having at least one cone region, and a body region respectively, which define corresponding portions of said balloon, and wherein said radial cross-section is taken in said body region of said interior cavity.

14. The method of claim 1 wherein the body region of the second mold form has a perimeter which is about 5% to about 30% larger than the body region of the first mold form.

15. The method of claim 13 wherein said second mold form has a configuration wherein said body region of said second mold form has two wings, three wings, four wings, five wings or six wings.

16. The method of claim 15 wherein said wings extend into the cone regions, the waist regions or both of said second mold form.

17. The method of claim 13 wherein said second mold form has a longitudinal axis and wherein said body region of said second mold form has a three wing configuration wherein each wing is spaced at 120 degrees about a longitudinal axis.

18. The method of claim 15 the cone region of the second mold form has a two wing, three wing, four wing, five wing or six wing configuration corresponding to said body region.

19. The method of claim 1 wherein said second mold form has a longitudinal axis and said body region of said second mold form has a five wing configuration wherein each wing is spaced at 72 degrees about a longitudinal axis.

* * * * *